United States Patent
Cheslock

(10) Patent No.: US 10,969,610 B2
(45) Date of Patent: Apr. 6, 2021

(54) METHOD AND APPARATUS FOR STORING, PRESERVING AND CLEANING CONTACT LENSES

(71) Applicant: William Cheslock, Longview, WA (US)

(72) Inventor: William Cheslock, Longview, WA (US)

( * ) Notice: Subject to any disclaimer, the term of this patent is extended or adjusted under 35 U.S.C. 154(b) by 0 days.

(21) Appl. No.: 16/738,931

(22) Filed: Jan. 9, 2020

(65) Prior Publication Data

US 2020/0150461 A1 May 14, 2020

Related U.S. Application Data

(63) Continuation of application No. 16/164,565, filed on Oct. 18, 2018, now Pat. No. 10,578,890.

(60) Provisional application No. 62/574,072, filed on Oct. 18, 2017.

(51) Int. Cl.
    *A45C 11/00*     (2006.01)
    *G02C 13/00*     (2006.01)
    *A61L 12/06*     (2006.01)

(52) U.S. Cl.
    CPC .......... *G02C 13/008* (2013.01); *A45C 11/005* (2013.01); *A61L 12/063* (2013.01)

(58) Field of Classification Search
    USPC ............................................ 206/5.1; 422/24
    See application file for complete search history.

(56) References Cited

U.S. PATENT DOCUMENTS

| | | | | |
|---|---|---|---|---|
| 5,120,499 A * | 6/1992 | Baron | ................... | A61L 12/026 250/455.11 |
| 5,443,801 A * | 8/1995 | Langford | ........... | A61B 1/00059 422/294 |
| 7,038,219 B2 * | 5/2006 | Clark | ........................ | A23L 3/26 250/455.11 |
| 8,851,091 B2 * | 10/2014 | Francavilla | ........... | A61L 12/128 134/113 |
| 8,881,892 B1 * | 11/2014 | Linhardt | ................ | B65D 77/08 206/5.1 |
| 9,789,220 B2 * | 10/2017 | Pugh | ...................... | A61L 12/063 |
| 2002/0117405 A1 * | 8/2002 | Wang | ................... | B65D 5/4216 206/5.1 |
| 2015/0173474 A1 * | 6/2015 | Barrows | ................ | B65D 81/22 206/5.1 |

* cited by examiner

*Primary Examiner* — Jacob K Ackun
(74) *Attorney, Agent, or Firm* — Mark E. Beatty; Rylander & Associates P.C.

(57) ABSTRACT

An apparatus for storing, preserving and cleaning contact lenses includes a base housing; one or more lens bowls transparent to selected ranges of UV and IR light wavelengths; UV and IR light sources to direct UV and IR light into the lens bowls; a removable cover opaque to the UV light; one or more closure sensors to sense the status of the cover; a power supply; and, a controller in control communication with the UV and IR light sources, the power supply and the closure sensors, the controller causing the UV and IR light sources to cease emitting when the cover is not closed.

16 Claims, 10 Drawing Sheets

METHOD AND APPARATUS FOR STORING, PRESERVING AND CLEANING CONTACT LENSES

CROSS-REFERENCE TO RELATED APPLICATIONS

This Application is a continuation of U.S. application Ser. No. 16/164,565, filed Oct. 18, 2018 which is a nonprovisional of, and claims priority to, U.S. Provisional Application Ser. No. 62/574,072, filed Oct. 18, 2017. This Application claims priority to both application Ser. No. 16/164,565 and Application 62/574,072.

FIELD OF THE INVENTION

The present invention relates to storing, cleaning and preserving contact lenses and other apparatus which may be used on the ocular surface, without specialized chemicals.

BACKGROUND

The current conventional method for cleaning, sterilization and storage of contact lenses generally requires chemicals. Chemical cleaning and sterilization is both inconvenient and can cause adverse reactions in users with sensitivities to the chemicals. The inconvenience of selecting and purchasing chemical solutions which are compatible with the particular lenses and do not cause adverse reactions in the users, over long timespans, leads to users sometimes running out of the solutions and/or using incorrect solutions, which can lead to infections and/or adverse reactions in the users. Inadequate maintenance practices also shorten the useful life of lenses. Bacterial and viral populations in and on the lenses can develop resistance to chemicals. In addition, the requirement to use specific chemicals in specific order can lead to errors by users, which again lead to adverse results. For example, failure to properly clean lenses prior to chemical sterilization can lead to incomplete sterilization in areas where mucus and protein buildup can shield bacteria and viruses underneath those layers from the sterilizing chemicals, creating danger of infections and irritation of the eyes. Reliance on chemical methods is unreliable on a systemic level.

There is a need for compact, simple, reliable apparatus and methods which are essentially failsafe and easy for ordinary consumers to use, and which avoid growth of chemical-resistant bacteria and viruses.

SUMMARY AND ADVANTAGES

An apparatus for storing, preserving and cleaning contact lenses, includes a base housing; a first lens bowl configured to retain a first contact lens and volume of lens-compatible fluid, the first lens bowl composed of material transparent to a selected range of UV light wavelengths, the first lens bowl coupled to the base housing; a first UV light source proximate the first lens bowl and oriented to direct UV light into the first lens bowl; a removable cover, the cover configured to enclose and seal around at least the first lens bowl, the lens cover substantially opaque to the UV light; a first closure sensor disposed to sense the removable cover in a closed or a not-closed status; a power supply; and, a controller, the controller including software instructions, the controller in control communication with at least the UV light source, the power supply and the first closure sensor, wherein the controller causes the first UV light source to cease emitting when the first closure sensor indicates the removable cover is in the not-closed status.

The apparatus may include a first IR light source proximate the first lens bowl and oriented to direct IR light into the first lens bowl; the first lens bowl material additionally transparent to IR light; and, the controller additionally in control communication with the first IR light source.

The apparatus may include a first UV reflector disposed within the removable cover above the first lens bowl, the first UV reflector disposed to reflect the selected band of UV light toward the first lens bowl.

The apparatus may include a second lens bowl configured to retain a second contact lens and volume of lens-compatible fluid, the second lens bowl composed of material transparent to the selected range of UV light wavelengths, the second lens bowl coupled to the base housing; a second UV light source proximate the second lens bowl and oriented to direct UV light into the second lens bowl; the removable cover additionally configured to enclose and seal around the second lens bowl; and, the controller additionally in control communication with at least the second UV light source.

The apparatus may include a second IR light source proximate the second lens bowl and oriented to direct IR light into the second lens bowl; and, the controller additionally in control communication with the second IR light source.

The apparatus may include a plurality of closure sensors; and, the controller additionally in control communications with the plurality of closure sensors.

The apparatus provide for short term disinfection and/or long term storage.

The invention provides many advantages over existing apparatus and methods, including: (1) UV and IR cleaning is less likely to lead to chemically-resistant bacterial and viral strains; (2) the apparatus is compact and safe for home use; (3) it reduces need for chemical agents which may be used ineffectively by consumers and/or which can adversely affect sensitive eye tissues; (4) alleviates concern for out-of-date cleaning solutions; (5) reduced danger that air pockets trapped inside contact lenses will lead to incomplete cleaning due to lack of chemical cleaner contact; (6) use of LEDs provides for precise control of wavelength, intensity and heat addition; (7) design conserves energy usage allowing for compactness and portability; (8) automatic cycles, system monitoring and interlocks require less attention and interaction by the user, so enhance reliability of hygiene overall; and (9) it is noncontact, so improves sterility.

Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims. Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

REFERENCE NUMBERS USED IN DRAWINGS

Figure 1:
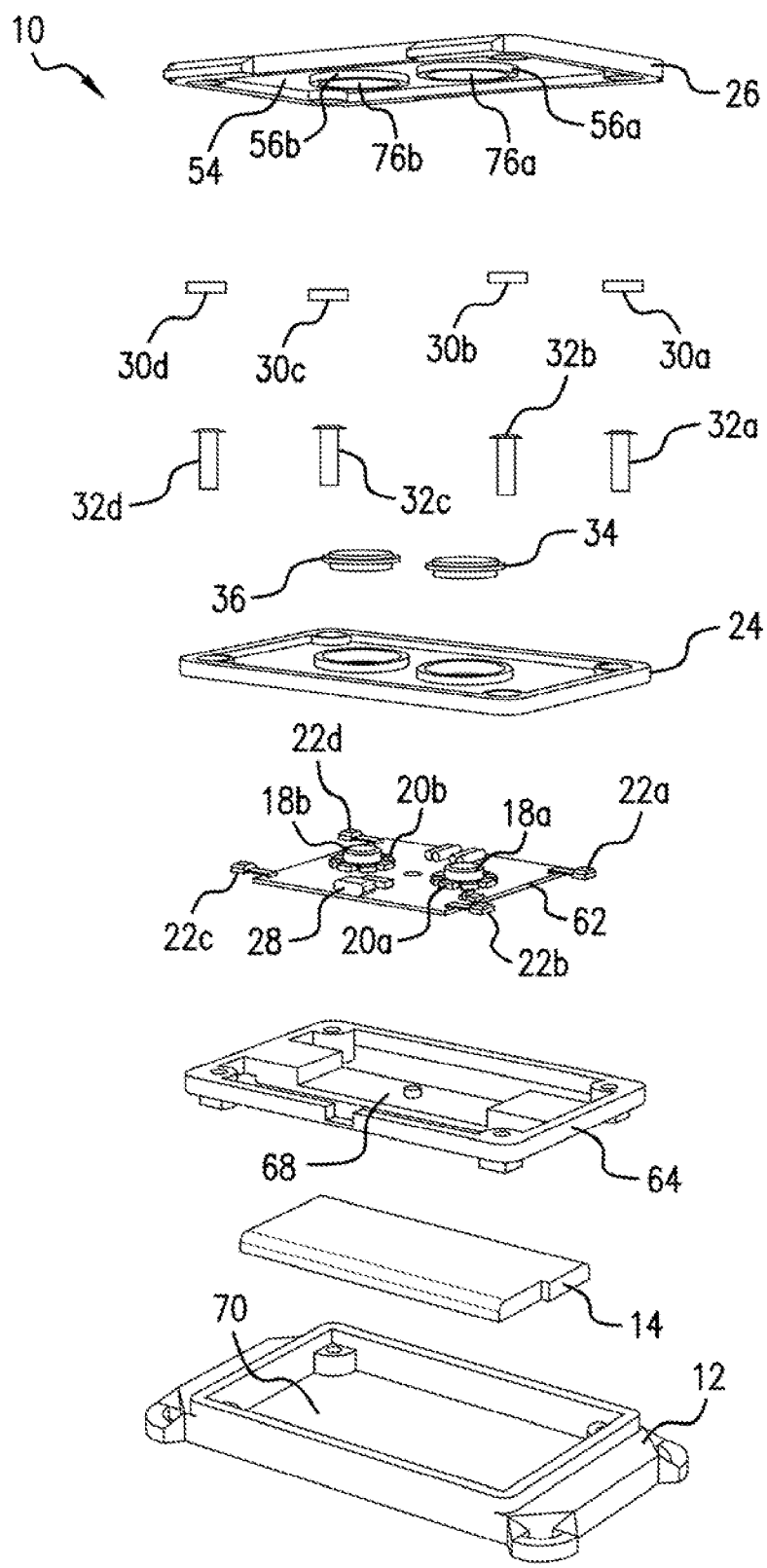
FIG. 1 shows an exploded view of a First Embodiment.
Figure 2:
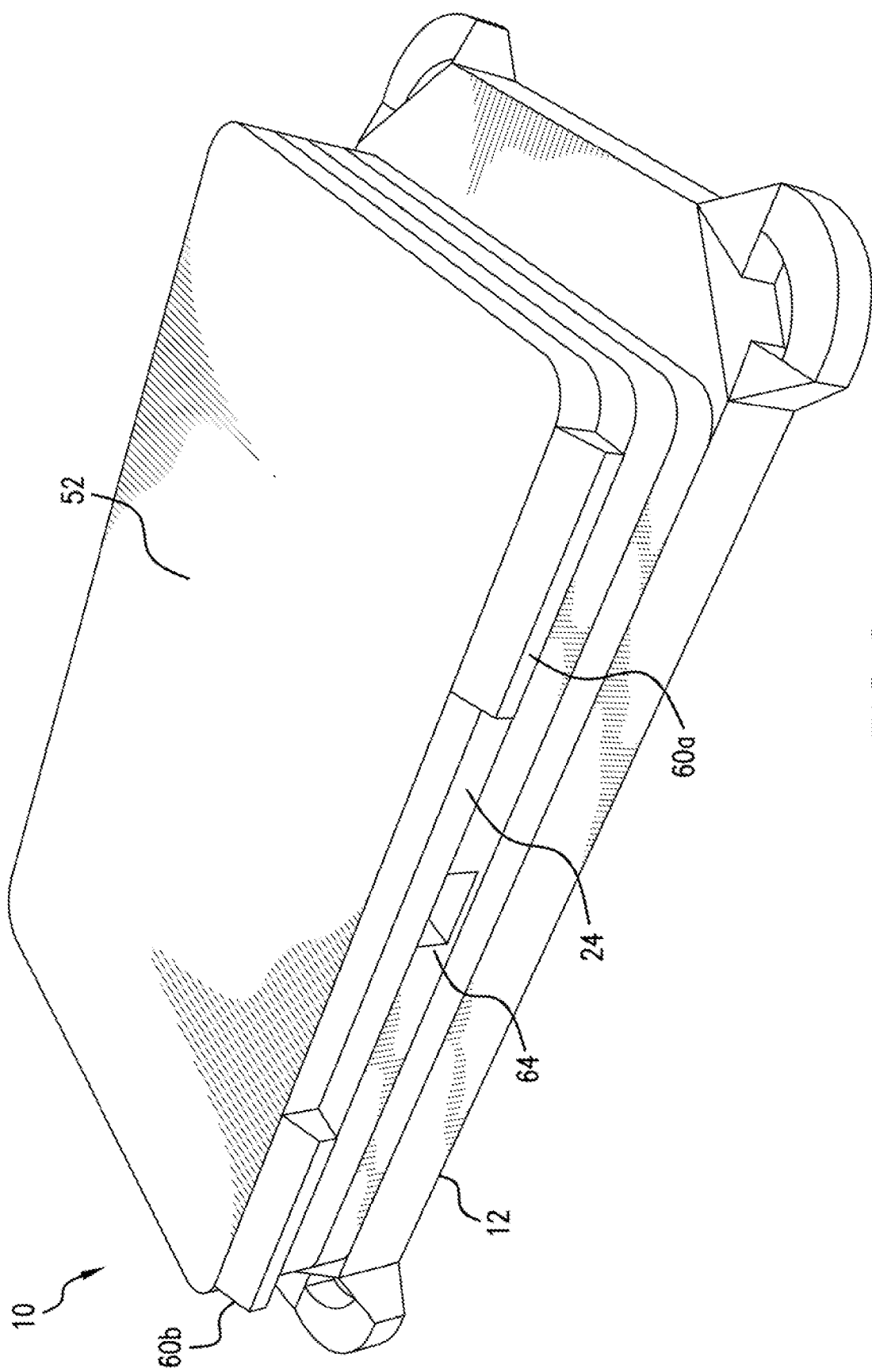
FIG. 2 shows a top perspective view of a First Embodiment, with cover closed.
Figure 3:
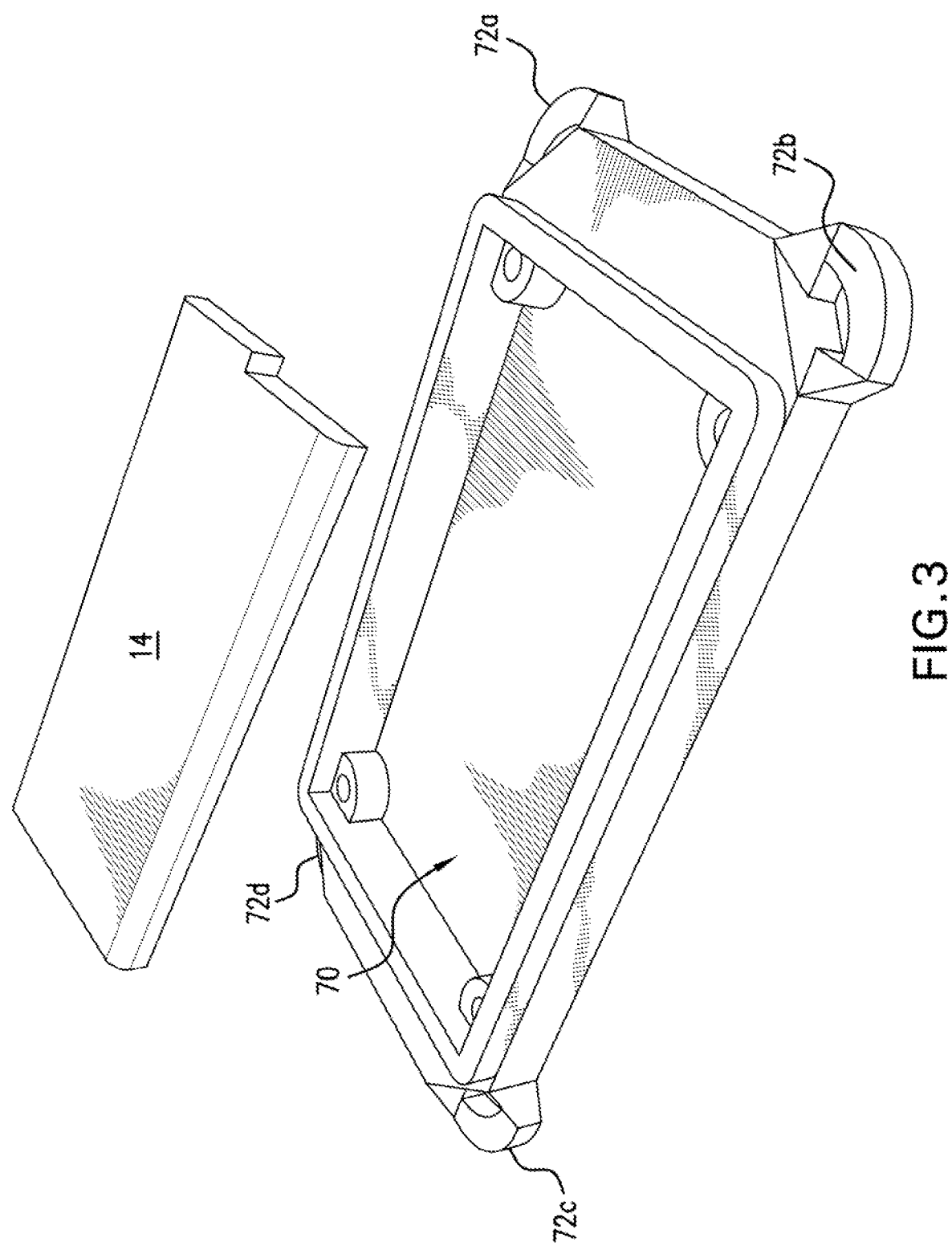
FIG. 3 shows a partial exploded view of a First Embodiment base housing and power supply.
Figure 4:
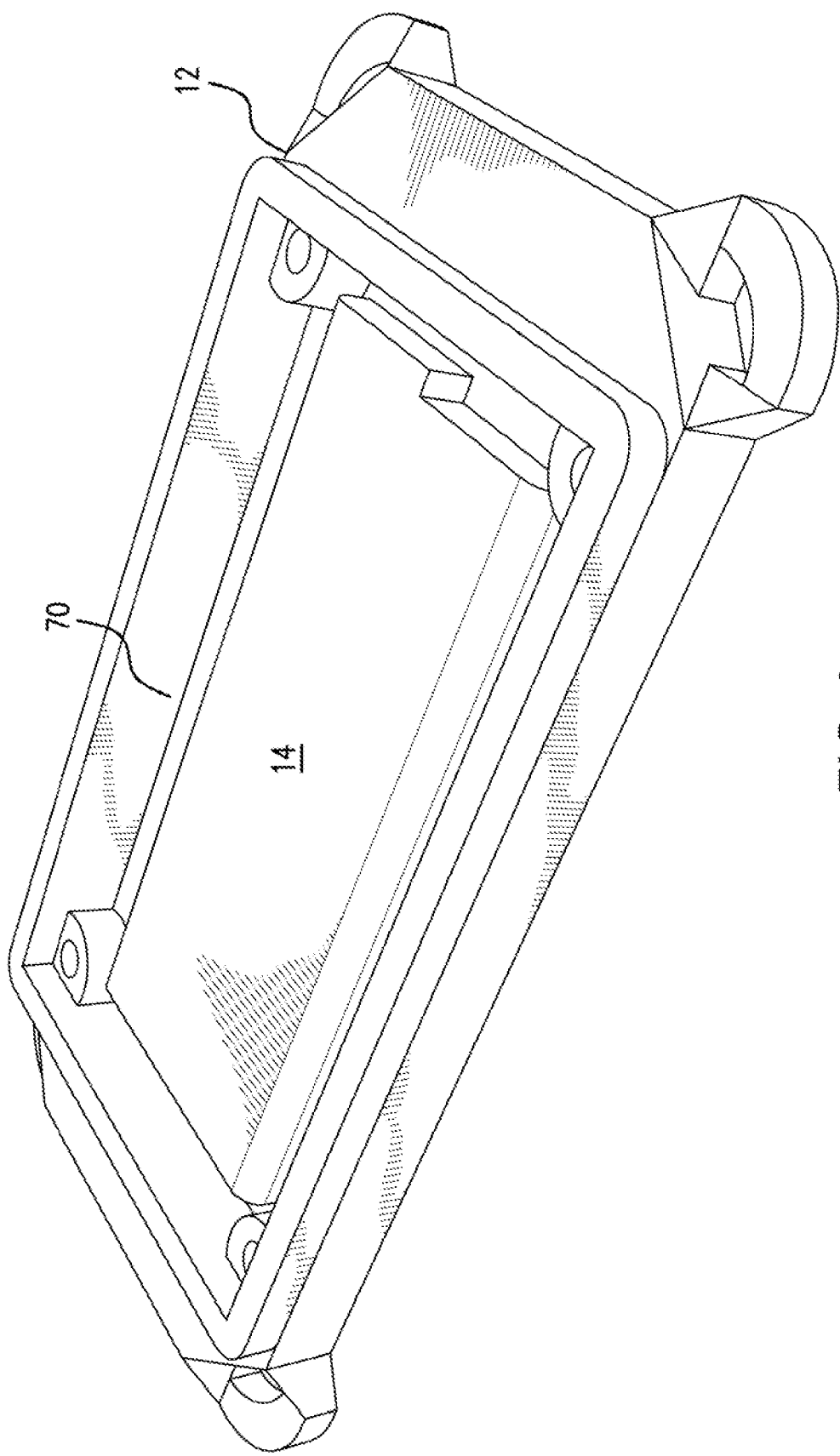
FIG. 4 shows a top perspective view of a base housing and power supply of a First Embodiment.
Figure 5:
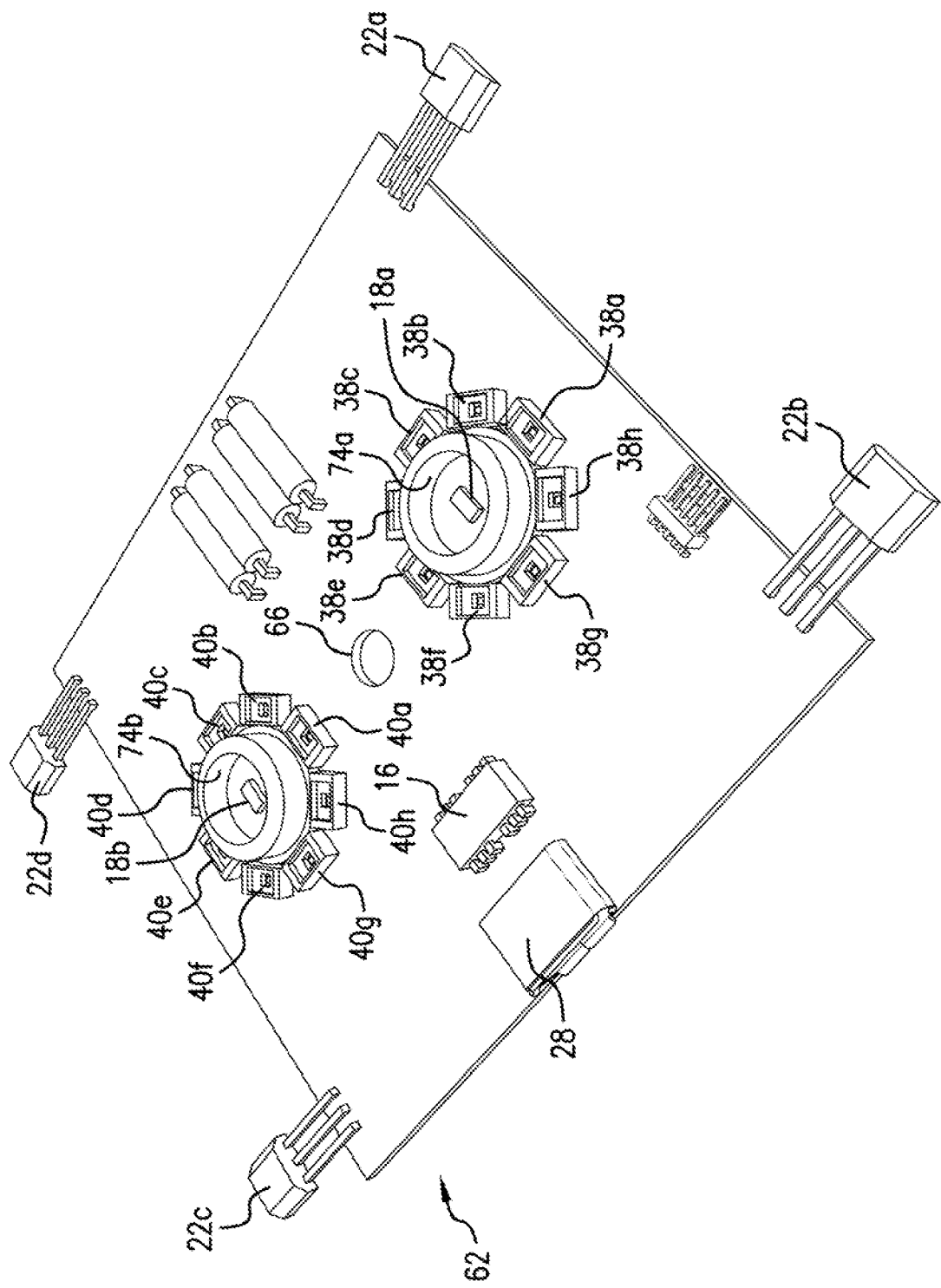
FIG. 5 shows a top perspective view of a PCB mounting board of a First Embodiment.
Figure 6:
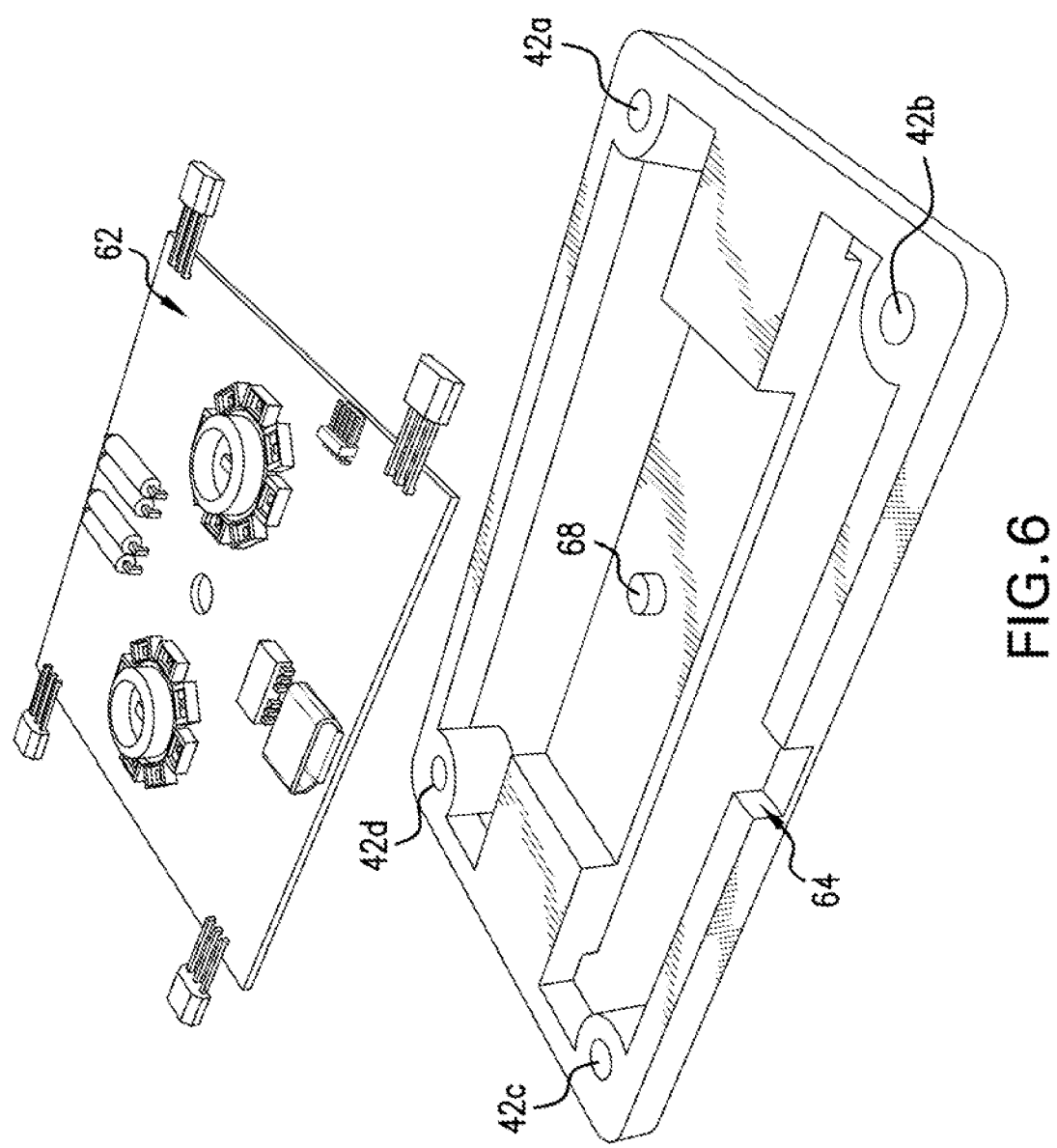
FIG. 6 shows partial exploded view of a First Embodiment PCB mounting board and electronic housing base.
Figure 7:
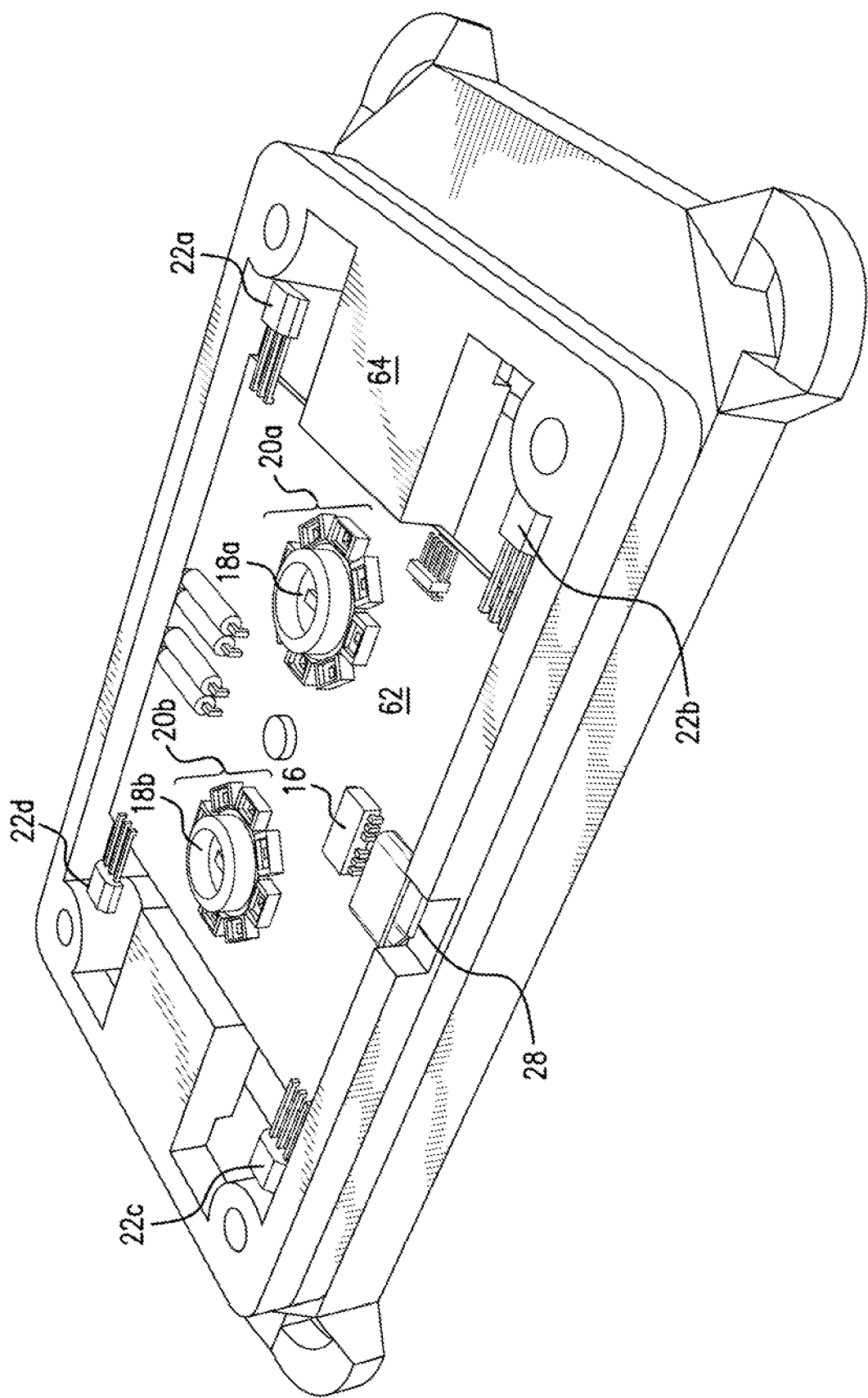
FIG. 7 shows a partially disassembled view of a base housing of First Embodiment with power supply and PCB mounting board installed.
Figure 8:
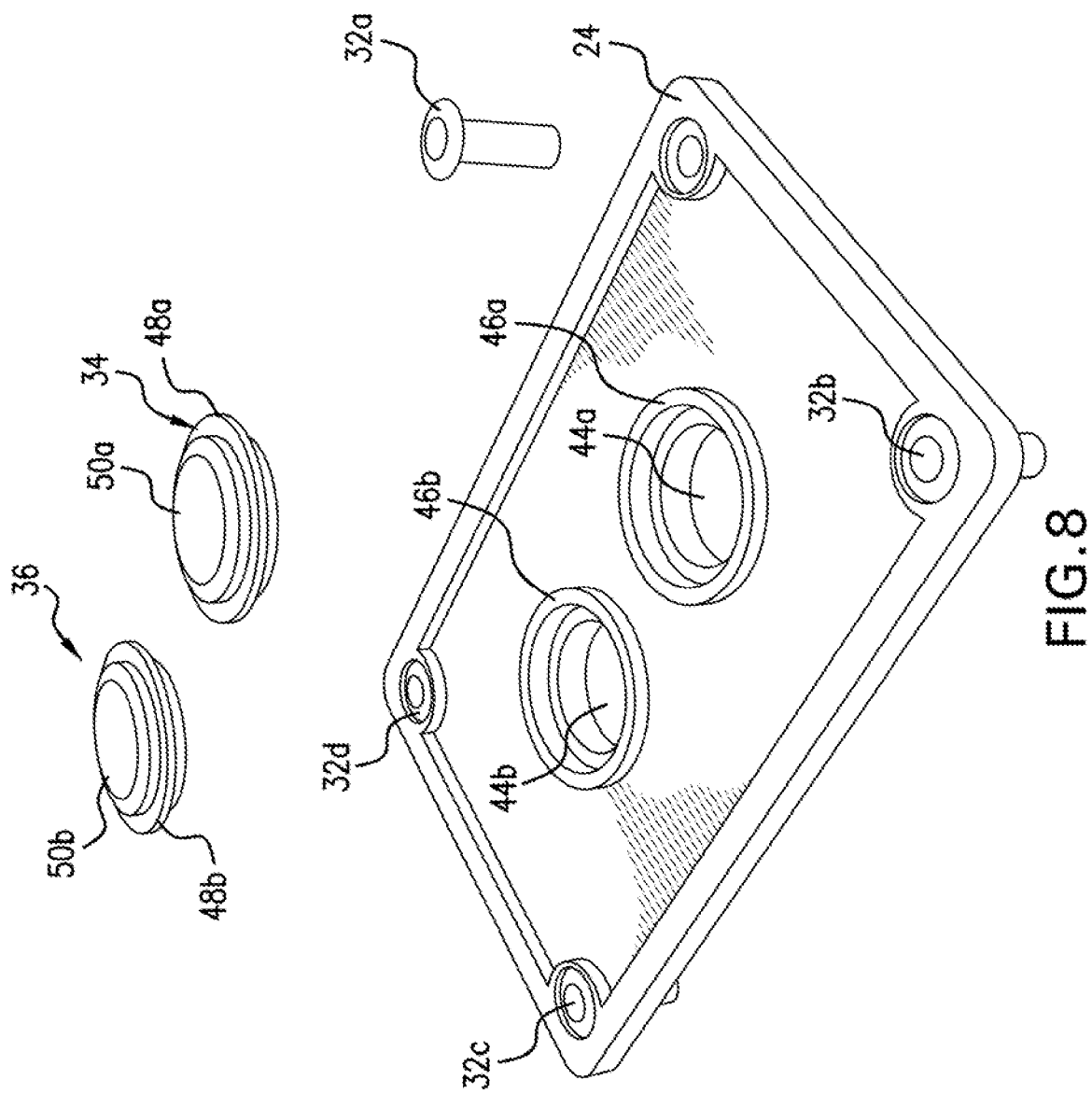
FIG. 8 shows a partial exploded view of a First Embodiment optical housing portion.
Figure 9:
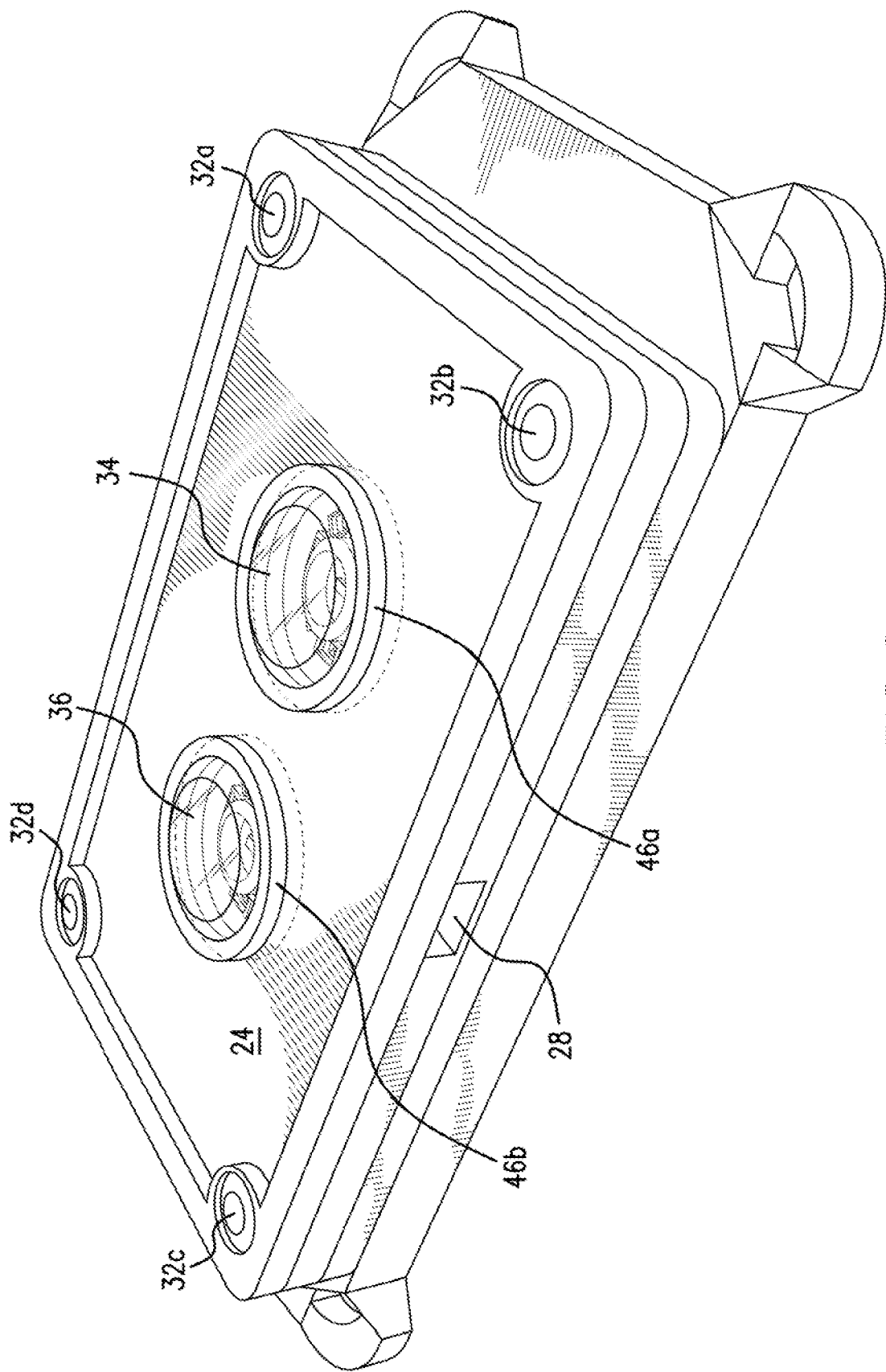
FIG. 9 shows a top perspective view of a First Embodiment without the cover.
Figure 10:
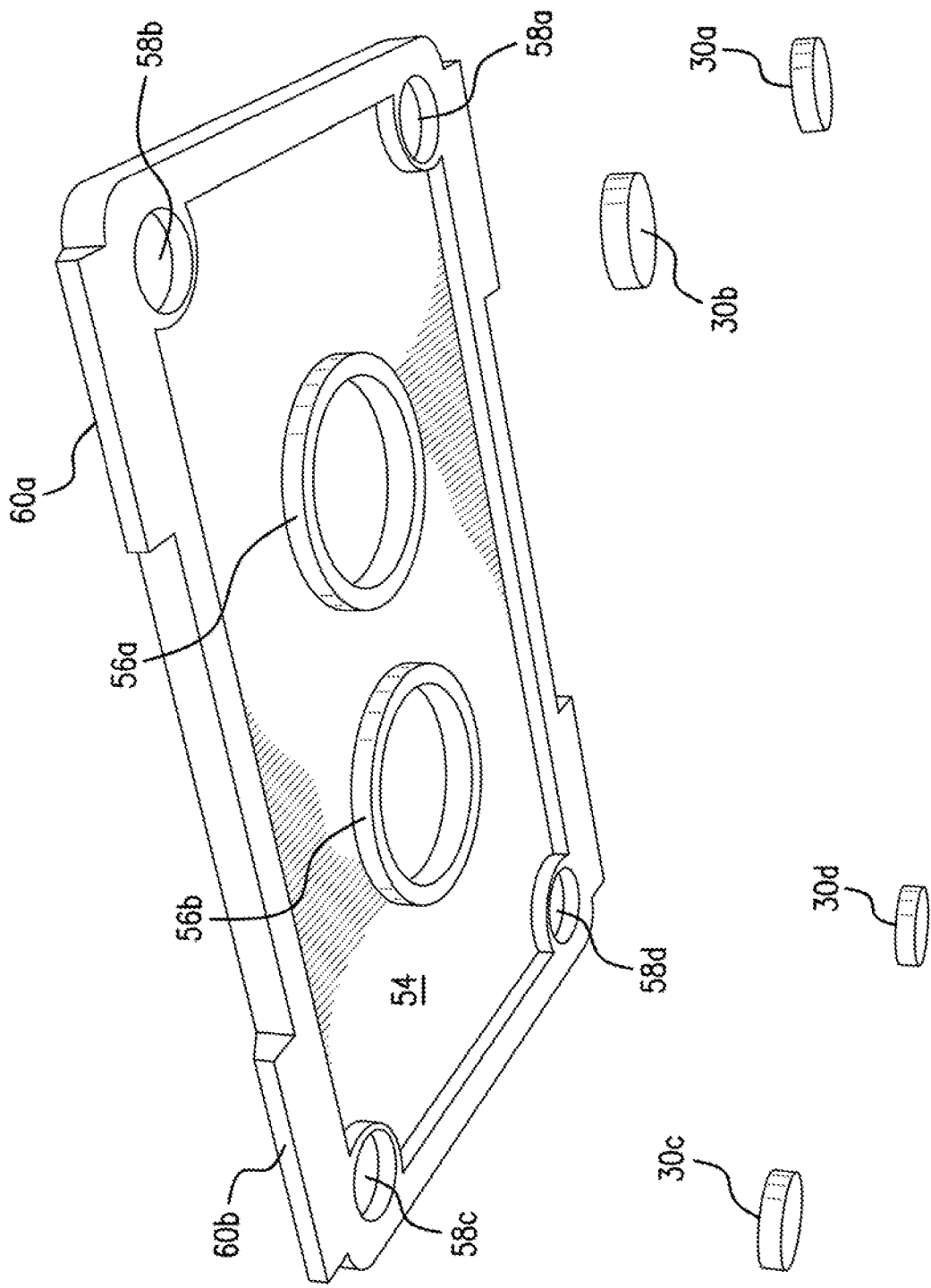
FIG. 10 shows a partial exploded view of a cover of a First Embodiment.

Turning now descriptively to the drawings, in which similar reference characters denote similar elements throughout the several views, the figures illustrate the present invention. With regard to the reference numerals used, the following numbering is used throughout the various drawing figures:

10 First Embodiment
12 Base Housing
14 Rechargeable Power Supply
16 Controller
18a First UV Light Source
18b Second UV Light Source
20a First IR Light Source
20b Second IR Light Source
22a First Closure Sensor
22b Second Closure Sensor
22c Third Closure Sensor
22d Fourth Closure Sensor
24 Optical Housing
26 Cover
28 Micro-USB Port
30a First Cover Closure Magnet
30b Second Cover Closure Magnet
30c Third Cover Closure Magnet
30d Fourth Cover Closure Magnet
32a First Magnetically Permeable Fastener
32b Second Magnetically Permeable Fastener
32c Third Magnetically Permeable Fastener
32d Fourth Magnetically Permeable Fastener
34 First Lens Bowl
36 Second Lens Bowl
38a IR LED Element
38b IR LED Element
38c IR LED Element
38d IR LED Element
38e IR LED Element
38f IR LED Element
38g IR LED Element
38h IR LED Element
40a IR LED Element
40b IR LED Element
40c IR LED Element
40d IR LED Element
40e IR LED Element
40f IR LED Element
40g IR LED Element
40h IR LED Element
42a First Optical Housing Fastener Aperture
42b Second Optical Housing Fastener Aperture
42c Third Optical Housing Fastener Aperture
42d Fourth Optical Housing Fastener Aperture
44a First Lens Bowl Aperture
44b Second Lens Bowl Aperture
46a First Lens Bowl Aperture Perimeter Ledge
46b Second Lens Bowl Aperture Perimeter Ledge
48a First Lens Bowl Perimeter Horizontal Flange
48b Second Lens Bowl Perimeter Horizontal Flange
50a First Lens Bowl Perimeter Vertical Flange
50b Second Lens Bowl Perimeter Vertical Flange
52 Cover Top/Outer Surface
54 Cover Bottom/Interior Surface
56a Cover First Sealing Flange
56b Cover Second Sealing Flange
58a First Closure Magnet Recess
58b Second Closure Magnet Recess
58c Third Closure Magnet Recess
58d Fourth Closure Magnet Recess
60a Cover First Finger Tab
60b Cover Second Finger Tab
62 PCB Mounting Board
64 Electronic Housing Base
66 PCB Mounting Board Alignment Aperture
68 PCB Mounting Board Alignment Pin
70 Power Supply Cavity
72a First Loop Extension
72b Second Loop Extension
72c Third Loop Extension
72d Fourth Loop Extension
74a First UV Light Source Sidewall
74b Second UV Light Source Sidewall
76a First UV Cover Reflector
76b Second UV Cover Reflector

DETAILED DESCRIPTION

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Referring to FIGS. 1-11, a first embodiment of an apparatus for storing, preserving and cleaning contact lenses are shown. Referring to FIG. 1, an exploded view of a first embodiment 10 is shown. First embodiment 10 includes a base housing 12, a power supply 14, an on-board controller 16, first and second UV light sources 18a & 18b, first and second IR light sources 20a & 20b, closure sensors 22a, 22b, 22c & 22d, optical housing 24, and cover 26.

In the First Embodiment, power supply 14 is a rechargeable lithium ion battery, coupled to micro-USB charging port 28 which includes a waterproof enclosure. A rechargeable power supply permits portability and flexibility. In the Embodiment, the apparatus 10 is usable both with the device unplugged and operating solely on battery power, or plugged in to another continuous power source—for example a wall outlet or power source in a vehicle. Rechargeable power supply 14 stores sufficient power for at least one complete cleaning cycle. Base housing 12 includes a power supply cavity 70 defining a space to retain rechargeable power supply 14.

Cover 26 includes a sealing engagement portion, and closure magnets 30a, 30b, 30c & 30d mounted within cover 26. Closure magnets help align cover 26 for proper closing and sealing, and magnetically couple to closure sensors 22a-d. Cover 26 may be made from a UV-absorbing material to prevent transmission of harmful levels of UV light, or may incorporate a UV-reflective surface. In the embodiment, cover 26 may also include first and second reflectors 76a & b, within first and second sealing flanges 56a & 56b. In the embodiment, first and second reflectors 76a & b are reflectors fixed to interior surface 54 within sealing flanges 56a & b, respectively, and having polished aluminum surfaces. First and second reflectors 76a & b may be coated to prevent corrosion and/or leaching. Reflectors may also be provided as applied reflective coatings on the interior surfaces.

Magnetically permeable fasteners 32a, 32b, 32c & 32d are provided, which perform two functions—engage with closure magnets, and provide magnetic coupling path for closure magnets to closure sensors 22a-d. In the embodiment, sensors 22a-d are Hall effect sensors, which require low power and produce low heat, are solid state, and noncontact, so easily sealed within the plastic casing, and will not interfere with the UV and IR LEDs. Fewer or more closure sensors could be used depending on the particular shape and configuration of the housing and cover, and closure sensors could be configured to sense the status of the cover as either the presence (i.e. closed and sealed status) or the absence (i.e. not completely closed or sealed status) of the cover. If at least one of closure sensors 22a-d senses the status of cover 26 as not-closed status, then the controller 16 will cause the UV light sources 18a & b and the IR light sources 20a & b to cease emitting. The apparatus could be programmed to permit operation with fewer than all closure sensors sensing a closed status where sufficient redundancy exists that fewer sensors would indicate complete closure.

In the Embodiment, first and second UV light sources 18a & b are hermetically sealed LEDs producing light in a narrow portion of the UV-C band, within a range of approximately 255 nm to 280 nm wavelength (which maximizes lethality to bacteria). The dosage absorbed by microorganisms within the storage compartment is a function of UV light intensity (or fluence rate) and exposure time, shown by the equation: Dose ($\mu w\text{-}s/cm^2$)=Intensity ($\mu w/cm^2$)×time (s). The required dosage to achieve 99% kill rate varies with the type of bacterial or virus, but typically a dose of approximately 8,000 $\mu w\text{-}s/cm^2$ would be required, with a minimum of 2,500 $\mu w\text{-}s/cm^2$. Use of sterile storage solution will reduce the dosage required to achieve and maintain satisfactory disinfection (i.e. the minimum microbial load). UV light sources 18a & b may include multiple UV LED elements. In the Embodiment, UV light sources 18a & b include first and second enclosing internally UV reflective sidewalls 74a & b, respectively, which contain and direct UV light into the respective first and second lens bowls 34, 36 but retain high transmittance for the selected IR wavelength band (in the described Embodiment, concentrated around the 650 nm wavelength).

In the embodiment, IR disinfection is combined with the UV disinfection to achieve optimum results. Each of first and second lens bowls 34 and 36 is centered within first and second IR light sources 20a & b, respectively, each of which includes eight IR LED elements, 38a-h and 40a-h, respectively, distributed evenly along a circular circumference. IR LED elements 38a-h and 40a-h produce light concentrated around the 650 nm wavelength to heat the water volume and any microbes and viruses therein. In the embodiment, the eight low power LED elements 38a-h and 40a-h distributed around each lens bowl 34 and 36 provide even heating of the compartment, while reducing the danger of structural damage/plastic melting from a lower number of higher power LED elements. IR LED elements 38a-h and 40a-h are selected to achieve a steady state operating temperature of at least 45 C-50 C (113 F-122 F) during the cleaning cycle. The IR LED elements 38a-h and 40a-h are deenergized prior to the end of the cleaning cycle, in order to allow the storage solution (and hence, the lenses) to cool to a comfortable temperature prior to removal. In the embodiment, IR LED elements 38a-h and 40a-h are relatively low power, each IR light source 20a & b sufficient to warm lens bowls 34 and 36 at steady state but not sufficient to damage the apparatus or lenses even if energized continuously, so as to obviate the need for complicated temperature feedback control. The total IR LED element power will be determined by the wall thickness of the specific materials selected and shape of the device to account for balancing heat losses.

In the Embodiment, controller 16 is an integrated circuit module mounted to PCB mounting board 62, which includes the L.E.D. drivers which control power to UV light sources 18a & b and IR light sources 20a & b, and monitor their operation, as well as the battery charging and management subsystem. Controller 16 also includes software instructions in the programable memory which, among other functions, control the process cycle, including the power level of the LED elements, timing, sequence and ramp up, system power management, safety interlock inputs, alarms and warnings, and system operation logs.

In the Embodiment, optical housing 24 is a planar element having fastener apertures 42a, 42b, 42c & 42d to receive magnetically permeable ferrous fasteners 32a-d, and first and second lens bowl apertures 44a & b, to receive first and second lens bowls 34 & 36. Lens bowl apertures 44a & b, are aligned to center lens bowls 34 & 36 over first and second UV light sources 18a & b, respectively. Lens bowl apertures 44a & b include perimeter ledges 46a & b, respectively. First and second lens bowls 34 & 36 are curved hemispherical or hyperbolically shaped bowls, each including a perimeter horizontal flange 48a & 48b, respectively, which couples with first and second lens bowl aperture perimeter ledges 46a & b, respectively. They may be sealed in place by, for example, gluing, or thermal or sonic welding. Lens bowls 34, 36 are made from optically clear, UV-C-transparent material, for example quartz-glass or UV-C-transparent acrylics, which have at least 80% transmittance at the selected wavelength or at least at the most desired wavelength within the selected range. In the embodiment, lens bowls 34, 36 themselves act as refractive lenses, in order to focus the UV light through a contact lens held within it and provide uniform UV transmittance and heat distribution. First and second lens bowl perimeter vertical flanges 50*a* & *b* extend upward from first and second lens bowls 34, 36, respectively, to engage cover 26. The shape and dimensions of lens bowls 34 and 36 are configured to receive a selected type and size of contact lens. In the Embodiment, lens bowls 34 and 36 are configured to receive the standard range of contact lenses used by people. Contact lenses used for animals may be larger or smaller than those used by people, and potentially shaped differently, so the dimensions of the bowls would be configured for the anticipated range of sizes and shapes for the type of use.

Cover 26 goes over the top of the apparatus to both seal lens bowls 34 & 36, and to shield a user from UV light sources 18*a* & *b*. In the Embodiment, cover 26 is substantially planar, having a top/outer surface 52 and a bottom/interior surface 54, and includes first and second sealing flanges 56*a* & 56*b* projecting from bottom/interior surface 54 to sealingly engage first and second lens bowl perimeter vertical flanges 50*a* & *b* and perimeter horizontal flanges 48*a* & *b*, respectively. Cover 26 also includes first, second, third and fourth closure magnet recesses 56*a*, 56*b*, 56*c* and 56*d* to retain closure magnets 30*a-d*, respectively. Closure magnet recesses 56*a-d* are located in a pattern matching magnetically permeable fasteners 32*a-d* to magnetically couple to them. Cover 26 includes first and second finger tabs 60*a* & 60*b* extending outward from its perimeter to provide easier grip for removal/installation.

In the Embodiment, UV light sources 18*a* & *b*, IR light sources 20*a* & *b*, micro-USB port 28, and associated controllers, drivers and circuitry, are mounted to a single planar PCB mounting board 62, which is sealed to prevent moisture damage. Closure sensors 22*a-d* are disposed proximate the four corners of PCB mounting board 62, aligned to be proximate to fastener apertures 42*a-d*. Micro-USB port 28 provides connection to external power, programming and monitoring/diagnostic devices.

PCB mounting board 62 is mounted onto electronic housing base 64, and includes an alignment aperture 66 to receive a corresponding alignment pin 68 therethrough to ensure proper positioning of closure sensors 22*a-d* and the UV & IR light sources 18*a* & *b* and 20*a* & *b*.

The apparatus could be configured as a single lens device as well, for example by omitting the second lens bowl and associated elements, and could be configured with more than two lens bowls for higher volume applications; however, typical applications would likely be a dual-lens configuration.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

I claim:

1. An apparatus for storing, preserving and cleaning contact lenses, comprising:
a base housing;
a first lens bowl configured to retain a first contact lens and volume of lens-compatible fluid, the first lens bowl composed of material transparent to a selected range of UV light wavelengths, the first lens bowl coupled to the base housing;
a first enclosing sidewall, the first enclosing sidewall including an interior surface, the first enclosing sidewall extending upward from the base housing, and a first UV light source mounted within the first enclosing sidewall proximate the first lens bowl and oriented to direct UV light into the first lens bowl, the first enclosing sidewall including a UV-reflective surface along its interior surface;
a removable cover, the cover configured to enclose and seal around at least the first lens bowl, the lens cover substantially opaque to the UV light;
a first closure sensor disposed to sense the removable cover in a closed or a not-closed status;
a power supply; and,
a controller, the controller including software instructions, the controller in control communication with at least the UV light source, the power supply and the first closure sensor, wherein the controller causes the first UV light source to cease emitting when the first closure sensor indicates the removable cover is in the not-closed status.

2. The apparatus of claim 1, further comprising:
a first IR light source proximate the first lens bowl and oriented to direct IR light into the first lens bowl;
the first lens bowl material additionally transparent to IR light; and,
the controller additionally in control communication with the first IR light source.

3. The apparatus of claim 1, further comprising:
a first UV reflector disposed within the removable cover above the first lens bowl, the first UV reflector disposed to reflect the selected band of UV light toward the first lens bowl.

4. The apparatus of claim 1, further comprising:
a second lens bowl configured to retain a second contact lens and volume of lens-compatible fluid, the second lens bowl composed of material transparent to the selected range of UV light wavelengths, the second lens bowl coupled to the base housing;
a second enclosing sidewall, the second enclosing sidewall including an interior surface, the second enclosing sidewall extending upward from the base housing, and a second UV light source mounted within the second enclosing sidewall proximate the second lens bowl and oriented to direct UV light into the second lens bowl the second enclosing sidewall including a UV-reflective surface along its interior surface;
the removable cover additionally configured to enclose and seal around the second lens bowl; and,
the controller additionally in control communication with at least the second UV light source.

5. The apparatus of claim 2, further comprising:
a second lens bowl configured to retain a second contact lens and volume of lens-compatible fluid, the second lens bowl composed of material transparent to the selected range of UV light wavelengths, the second lens bowl coupled to the base housing;
a second enclosing sidewall, the second enclosing sidewall including an interior surface, the second enclosing sidewall extending upward from the base housing, and a second UV light source mounted within the second enclosing sidewall proximate the second lens bowl and oriented to direct UV light into the second lens bowl, the second enclosing sidewall including a UV-reflective surface along its interior surface;

a second IR light source proximate the second lens bowl and oriented to direct IR light into the second lens bowl;

the removable cover additionally configured to enclose and seal around the second lens bowl; and, the controller additionally in control communication with at least the second UV light source and the second IR light source.

6. The apparatus of claim 5, further comprising:
a plurality of closure sensors; and,
the controller additionally in control communications with the plurality of closure sensors.

7. The apparatus of claim 2, further comprising:
a first UV reflector disposed within the removable cover above the first lens bowl, the first UV reflector disposed to reflect the selected band of UV light toward the first lens bowl.

8. The apparatus of claim 4, further comprising:
a second UV reflector disposed within the removable cover above the second lens bowl, the second UV reflector disposed to reflect the selected band of UV light toward the second lens bowl.

9. The apparatus of claim 5, further comprising:
a second UV reflector disposed within the removable cover above the second lens bowl, the second UV reflector disposed to reflect the selected band of UV light toward the second lens bowl.

10. The apparatus of claim 3, further comprising:
a plurality of closure sensors; and,
the controller additionally in control communications with the plurality of closure sensors.

11. The apparatus of claim 4, further comprising:
a plurality of closure sensors; and,
the controller additionally in control communications with the plurality of closure sensors.

12. The apparatus of claim 7, further comprising:
a plurality of closure sensors; and,
the controller additionally in control communications with the plurality of closure sensors.

13. The apparatus of claim 8, further comprising:
a plurality of closure sensors; and,
the controller additionally in control communications with the plurality of closure sensors.

14. The apparatus of claim 9, further comprising:
a plurality of closure sensors; and,
the controller additionally in control communications with the plurality of closure sensors.

15. The apparatus of claim 13, further comprising:
a plurality of UV reflectors, each UV reflector disposed within the removable cover above a respective lens bowl, each UV reflector disposed to reflect the selected band of UV light toward the respective lens bowl.

16. An apparatus for storing, preserving and cleaning contact lenses, comprising:
a base housing;
a plurality of lens bowls, each configured to retain a contact lens and volume of lens-compatible fluid, each lens bowl composed of material transparent to a selected range of UV light wavelengths, each lens bowl coupled to the base housing;
a plurality of UV light sources, each UV light source mounted proximate a respective lens bowl and oriented to direct UV light into the respective lens bowl;
a plurality of IR light sources, the plurality of IR light sources mounted proximate a respective lens bowl and oriented to direct IR light into the respective lens bowl, the material of each of the plurality of lens bowls additionally substantially transparent to IR light; and,
a removable cover, the cover configured to enclose and seal around at least the plurality of lens bowls, the lens cover substantially opaque to the UV light;
at least one closure sensor disposed to sense the removable cover in a closed or a not-closed status;
a power supply; and,
a controller, the controller including software instructions, the controller in control communication with at least the plurality of UV light sources, the plurality of IR light sources, the power supply and the at least one closure sensor, wherein the controller causes the respective UV light sources to cease emitting when the at least one closure sensor indicates the removable cover is in the not-closed status.

* * * * *